United States Patent
Talanov et al.

(10) Patent No.: US 6,366,096 B1
(45) Date of Patent: Apr. 2, 2002

(54) APPARATUS AND METHOD FOR MEASURING OF ABSOLUTE VALUES OF PENETRATION DEPTH AND SURFACE RESISTANCE OF METALS AND SUPERCONDUCTORS

(75) Inventors: Vladimir V. Talanov, Greenbelt; Steven Mark Anlage, Laurel, both of MD (US)

(73) Assignee: University of Maryland, College Park, Riverdale, MD (US)

( * ) Notice: Subject to any disclaimer, the term of this patent is extended or adjusted under 35 U.S.C. 154(b) by 0 days.

(21) Appl. No.: 09/633,252

(22) Filed: Aug. 4, 2000

Related U.S. Application Data (60) Provisional application No. 60/147,705, filed on Aug. 6, 1999.

(51) Int. Cl.[7] ................................................ G01R 27/00
(52) U.S. Cl. ........................ 324/633; 324/653; 324/662
(58) Field of Search ................................ 324/234, 236, 324/237, 633, 636, 71.6, 652, 653, 655, 662, 635

(56) References Cited

U.S. PATENT DOCUMENTS

| | | |
|---|---|---|
| 3,745,479 A | 7/1973 | Okabe et al. |
| 4,918,050 A | 4/1990 | Dworsky |
| 4,959,614 A | 9/1990 | Bowling et al. |
| 4,968,945 A | 11/1990 | Woskov et al. |
| 5,239,369 A | 8/1993 | Suzuki |
| 5,268,646 A | 12/1993 | Doss |
| 5,420,518 A * | 5/1995 | Schafer ...................... 324/653 |
| 5,496,797 A | 3/1996 | Higaki et al. |
| 5,506,497 A | 4/1996 | Klein et al. |
| 5,563,505 A | 10/1996 | Dorothy et al. |
| 5,710,105 A | 1/1998 | Shen |
| 6,025,725 A * | 2/2000 | Gershenfeld et al. ....... 324/652 |

* cited by examiner

Primary Examiner—Safet Metjahic
Assistant Examiner—Vincent Q. Nguyen
(74) Attorney, Agent, or Firm—Rosenberg, Klein & Lee (57) ABSTRACT

An apparatus and method for accurately estimating the absolute value of surface resistances and penetration depths of metallic films and bulk samples. The apparatus carries out measurements using two nominally identical samples with flat sample surfaces which are brought together with a thin dielectric separation of variable thickness sandwiched between the samples in order to form a two-conductor parallel plate transmission line resonator which carries an electromagnetic wave. A liquid or gas of unknown dielectric properties fills the dielectric spacer. A resonant condition of the microwave signal is established and the resonant frequency and the quality factor Q are measured while the spacing between the sample plates is varied. The variation of the resonant frequency and Q with spacer thickness is then analyzed to yield absolute values of the sample surface resistance and penetration depth which are then further used for determination of absolute complex conductivity and surface impedance of the samples.

20 Claims, 5 Drawing Sheets

APPARATUS AND METHOD FOR MEASURING OF ABSOLUTE VALUES OF PENETRATION DEPTH AND SURFACE RESISTANCE OF METALS AND SUPERCONDUCTORS

REFERENCE TO RELATED APPLICATION

This Patent Application is based upon U.S. Provisional Application Ser. No. 60/147,705 provisional application has been expired, filed Aug. 6, 1999.

This invention was made with Government support and funding from NSF NATO Postdoctoral Fellowship Visiting Scientist DGE-97-10702. The Government has certain rights in this invention.

FIELD OF THE INVENTION

The present invention relates to a technique adapted to perform accurate measurements of the metallic and dielectric properties of materials at microwave frequencies; and more particularly, to an apparatus and method for determining the absolute screening length (or penetration depth) and surface resistance of metals or superconductors, either films or bulk, absolute complex conductivity and surface impedance of metals and superconductors, as well as for determination of dielectric constants and loss tangent of gases and liquids.

The present invention further relates to a technique using a resonant structure formed of a pair of substantially identical samples under investigation which are positioned in substantially parallel relationship each with respect to the other having a dielectric spacer of variable thickness disposed between the samples. The resonant frequency and quality factor vs. the variable thickness of the dielectric spacer are measured to be inserted in predetermined mathematical formulas correlated to the type of the samples in order to extract the absolute values of penetration depths and surface resistance for the samples. Extracted values of penetration depths and surface resistance are further used for determination of absolute complex conductivity and surface impedance of metals and superconductors in both films and bulk materials.

BACKGROUND OF THE INVENTION

Investigation of the microwave surface impedance $Z_S = R_S + iX_S$ of superconductors has been given prominence. Much of such prior investigations has been based on the pioneering works of Pippard and has been invigorated by the discovery of high temperature superconductors (HTS). An additional impetus for the development has been the appearance of a new family of synthesized microwave sources and network analyzers which has enabled a number of techniques to be developed.

Most of these techniques provide accurate determinations of the absolute value of the surface resistance, $R_S$, and provide sensitive measurements of changes in the surface reactance $X_S = \mu_0 \omega \lambda$ or the magnetic penetration depth $\lambda$. However, there still exists the problem of experimentally determining the absolute value of $\lambda$ since it is small, possibly on the order of tens to hundreds of nanometers. In fact, unlike $R_S$ measurements, there is no well-established universal and commonly accepted technique for determining the absolute penetration depth in superconductors.

Investigation of superconducting surface impedance is important since it yields valuable information about intrinsic (charge carrier density, pairing state symmetry, quasiparticle excitation spectrum and relaxation time) and extrinsic properties (microstructure) of the specimen under study. These properties can be deduced from the surface impedance $Z_S = \sqrt{i\mu_0 \omega / \sigma}$ (local limit) measured as a function of temperature, applied magnetic field, doping, or impurity concentration, wherein $\mu_0$ is a constant of permeability of free space, and $\omega$ is an angular frequency of the field. The complex conductivity, $\sigma = \sigma_1 - i\sigma_2$, is a fundamental quantity which theories of superconductivity are able to calculate. However, the inability to determine both the surface resistance and the absolute value of $\lambda$ for the same sample often hampers effort to construct the complex conductivity from the surface impedance data. For example, the real part of the conductivity $\sigma_1$ can be extracted from $R_S$ only if the absolute $\lambda$ is available.

The appearance of low loss HTS epitaxial thin films on single crystal dielectric substrates has led to a growing field of superconducting wireless communication. In this respect, knowledge of the surface impedance is important to obtain the optimum performance of superconducting RF/microwave components and circuits. Another important issue is the establishment of a standard characterization technique for HTS thin films for microwave applications.

Existing experimental techniques suitable for measurement of absolute $\lambda$ in superconductive thin films and single crystals may be divided into the following four categories: absolute length scale techniques, reflection or transmission measurements of electromagnetic fields (mutual inductance, microwave/millimeter wave, infrared (IR) spectroscopy), measurement of internal magnetic field distribution (muon spin rotation [$\mu$SR], neutron scattering), and Josephson tunneling experiments. Each of these techniques will be described in the following paragraphs.

1. Absolute Length Scale Techniques

An optimum way to measure an absolute screening length in a superconducting (or normal metal) sample is to determine an absolute length scale, l, which is comparable to and directly linked to the absolute value of $\lambda$. Many of the existing techniques for measuring changes in $\lambda$ measure a signal proportional to the value of l–$\lambda$, hence the greater the $\lambda$/l ratio, the higher the sensitivity to the penetration depth. However, little effort has been made to measure an absolute $\lambda$ via determination of an absolute length scale due to the fact that in practice, the latter cannot be measured with sufficient accuracy.

The absolute length scale techniques are generally based on the effect of electromagnetic field exclusion in the Meissner state of a superconductor. For single crystals these include DC/AC magnetometry and RF/microwave resonator perturbation techniques. In all of them l is the specimen's linear dimension and the measured signal (for example, shift in the resonant frequency between the empty and perturbed resonator) is proportional to $(1-\gamma\lambda) \times$(area of the sample), where $\gamma \sim 1$ depends upon the sample geometry and the field configuration. Usually, for crystals $\lambda/l \sim 10^{-3} - 10^{-4}$ and the relevant calibration does not allow measurement of an absolute $\lambda$.

In the case of a resonator in which all or a substantial part of it is made up of the superconductive material, $l = \Gamma/\mu_0 \omega$, where $\Gamma$ is the resonator geometrical factor. The resonant frequency is $f_{SC} \approx f_0 (1-\lambda/2l)$, where $f_0$ is the frequency of the same perfectly conducting resonator. Cavity-like resonators, such as end-plates or dielectric resonators have l on the order of the wavelength of electromagnetic radiation and the ratio $\lambda/l \leq 10^{-4}$ is generally small.

Planar resonators, such as stripline or conventional parallel plates, carry a slowed-down electromagnetic wave with a phase velocity $c_{SW}=c/\sqrt{\in_{eff}(1+2\lambda/s)}$, where c is velocity of light in vacuum, $\in_{eff}$ is the effective dielectric constant of the transmission line, and s is the dielectric thickness. Each have a high sensitivity to the penetration depth (down to 0.1 nm), since $\lambda/l=2\lambda/s\sim 10^{-2}-10^{-4}$ in this case. However, neither the cavity-like nor planar resonators are suitable for direct measurement of absolute $\lambda$ (except possibly for the coplanar resonator), and only changes in $\lambda$ may be extracted from the experiment.

The most common way to evaluate an absolute $\lambda(T=0)$ using the above techniques involves fitting of the measured temperature dependence of the parameter relevant to the changes in $\lambda$ (commonly, shift in the resonant frequency) to a theoretical dependence for $\lambda(T)$ (a proper electrodynamic description of the experimental structure is required). Usually, this procedure works adequately for conventional superconductors where appropriate models (two fluid or BCS) for $\lambda(T)$ are well established. However, such models fail in the presence of extrinsic effects in the sample under study. In the case of HTS there is a lack of suitable models for $\lambda(T)$, and usually the absolute $\lambda$ values deduced from experiment are strongly dependent (up to 50%) on the form of the temperature model assumed.

The other three categories of techniques generally allow one to measure absolute $\lambda$ without the need to determine the absolute length scale. When combined with techniques of measuring the surface impedance, they allow reconstruction of the complex conductivity $\sigma$. However, it is most desirable to carry out the measurements of absolute $\lambda$ and $R_S$ within the same experimental arrangement and on the same sample.

2. Reflection/transmission of Electromagnetic Field

The mutual inductance technique is the most simple and accurate (to within a few percent) way to determine the penetration depth of thin films at low frequencies. It is based on the measurement of the mutual AC inductance of two axially symmetric coils separated by a superconducting film. This technique is usable for film thickness up to 1 $\mu$m for typical ($\lambda\sim300$ nm, sample linear size is 12 mm by 12 mm) HTS films. An accurate knowledge of the film thickness and its uniformity are required over the entire sample.

Microwave/millimeter wave reflection/transmission techniques are based on a measurement of S-parameters of a coaxial or cylindrical waveguide terminated by the superconductive sample (thin film). The absolute value of the reflection coefficient is close to unity and does not allow reliable measurement of absolute $\lambda$. The transmission coefficient is <<1 even for very thin films (down to d~$\lambda X_S/Z_0$), hence the absolute version of this method requires sophisticated calibration ($Z_0$ is the characteristic impedance of free space).

This problem can be eliminated in the case of relative transmission measurements, which in turn requires accurate knowledge of the sample normal state resistivity. Another typical complication for both methods is leakage of radiation around the sample. The transmission methods are generally limited to very thin films of homogeneous thickness.

In IR spectroscopy a Kramers-Kronig transform of the power reflectivity, measured over a wide range of frequency allows one to obtain $\sigma_2(\omega)$. The latter when extrapolated to the low-frequency limit $\sigma_2(\omega\approx 0)=1/\mu_0\omega\lambda^2$, provides the penetration depth. Alternatively the oscillator strength sum rule may be employed to obtain the strength of the zero frequency delta function response of the superconducting condensate. This technique has the advantage of working with very small samples (single crystals), and allows estimate of all three components of the penetration depth in anisotropic superconductors. However, this technique is very demanding technically and subject to uncertainty due to the finite frequency measurement range.

3. Probing of Internal Magnetic Field Distribution

The muon spin rotation/relaxation ($\mu$SR) technique is a powerful tool to determine the local magnetic field distribution in a superconductor. This technique has the advantage of providing bulk measurement of $\lambda$, but requires a detailed model of the superconducting mixed state.

Polarized neutron reflectometry (PNR) is based on the study of polarized neutron glancing angle reflection from the sample surface, which is sensitive to the screening of the external magnetic field inside a superconductor. Its advantage is sensitivity to the shape of the magnetic flux penetration profile itself, rather than just the penetrated magnetic flux. PNR has measured the absolute penetration depth in conventional superconductors (Nb). However, even for the best epitaxial HTS films available the overall surface topology is too poor to obtain $\lambda$ with sufficient precision.

4. Josephson Tunneling

The Josephson tunneling technique is based on modulation of the Josephson junction critical current by external magnetic field, and provides an accurate estimation of absolute $\lambda$. Its main limitation is requirement that a Josephson junction be made with the material of interest.

It is clear from the aforesaid that it would be highly desirable to have a technique for accurate determination of the absolute values of $\lambda$ and $R_S$, as well as absolute complex conductivity, surface impedance, and other parameters of metals and superconductors, free of the shortcomings of the prior methodologies and systems.

SUMMARY OF THE INVENTION

An object of the present invention is to provide a universal technique which can measure both the surface resistance and absolute value of the penetration depths in superconducting films, as well as the skin depth of normal metal using a variable spacing parallel plate resonator (VSPPR).

It is a further object of the present invention to provide a fully automated system for accurate measurements of metallic and dielectric properties of material at microwave frequencies both at room and cryogenic temperature.

It is still another object of the present invention to provide a technique in which a two-conductor electromagnetic resonant structure is formed of two identical samples separated by a dielectric spacer (which may be either liquid nitrogen, liquid helium, or vacuum), where one of the samples is displaced with respect to the other to vary the distance therebetween. During this displacement which is made in small increments, measurements of resonant frequency and the quality factor vs. the variable thickness of the dielectrical spacer are made. These measurements are further processed by inserting the measured values into mathematical formulae correlated with the type of the samples in order to extract therefrom absolute values of penetration depths and surface resistance for the samples which are further used for determining various metallic and dielectric properties of materials under investigation.

It is another object of the present invention to provide a unique displacement mechanism for the resonant structure formed of a pair of identical samples separated by a dielectric spacer which has practically unlimited resolution and substantially zero friction between the structure elements.

It is still a further object of the present invention to provide a technique for measuring the penetration depth and surface resistance of superconducting and metallic materials for both films and bulk in which a parallelism of the samples forming a resonant structure is achieved and maintained by means of flexible coupling mechanism by bringing the samples into intimate contact therebetween for self-aligning which obviates the need for glue or other adhesive.

The technique of the present invention is designed specifically to determine the absolute screening length (or penetration depth) and the absolute surface resistance of a metal (or superconductor) film or bulk material at microwave frequencies. These two quantities are further combined to determine the absolute complex conductivity and surface impedance of the material. The invention can also be used to determine the dielectric constant and loss of tangent of gases and liquids at microwave frequencies.

For this purpose, a resonator is formed by two parallel metallic or superconducting plates (bulk material or thin films on dielectric substrates) separated by a thin dielectric spacer forming an open ended transmission line resonator. An important concept of the technique of the present invention is to measure the resonant frequency, f, and the quality factor, Q, of the VSPPR versus the continuously variable thickness of the dielectric spacer, and to fit the measured data into theoretical forms in order to extract the absolute values of $\lambda$ and $R_S$ therefrom.

The measurements are carried out using two nominally identical samples with flat face surface—film and/or bulk metal and/or superconductor. The samples are positioned face-to-face to sandwich a thin dielectric separation (dielectric spacer) of variable thickness from 0 to 200 $\mu$m. The material filling the dielectric spacer may include liquid nitrogen, liquid helium, vacuum, or other liquid or gas. The dielectric properties of the dielectric spacer are not necessarily known. This combination forms a 2-conductor parallel plate transmission line resonator—Variable Parallel Plate Resonator (VPPR) which carries a quasi-TEM electromagnetic wave.

The Q-factor and resonant frequency of the resonator are dictated by its geometry, as well as by the ratio between the dielectric spacer thickness and the screening (penetration) depth in the samples. The losses in the resonator are determined by dielectric loss in the dielectric spacer matter, radiation losses, and the surface resistance of the samples. The first two contributions may be measured directly using a calibration procedure and/or eliminated by using disc-shape resonator with TM00i (where i is an integer) mode and vacuum dielectric spacer. The measured Q-factors can be corrected to reflect only the contribution of the surface resistance losses.

Accurate estimation of the absolute value of the penetration depth and surface resistance is based on the simultaneous analysis of spacer thickness dependencies of the resonator frequency f and the Ohmic quality factor O in association with the electrodynamics theory of the resonator.

The apparatus for measurements includes the Cryogenic Slider, Linear Actuator, Film Aligner and Microwave Coupling Probes.

The Cryogenic Slider is made from two coaxial thin-wall stainless steel tubes with the flexure-type bearings incorporated between the inner and outer tubes at both the top and bottom ends of the slider. One of the tubes, such as the outer tube, is fixed, while the other tube, such as the inner one, translates along the vertical axis driven by the Linear Actuator connected to the top of the slider. Bearings of special shape are made from Cu/Be foil and work either at room or at cryogenic temperature. They provide 1-mm of full travel while substantially reducing friction and theoretically giving resolution limited only by thermal fluctuations.

The top of the slider is maintained at room temperature; the bottom is maintained at cryogenic conditions (4÷77 K). To compensate for thermal contraction during the experiment, the tubes are made to be of the same length and from the same material (stainless steel).

From a kinematics point of view the Film Aligner is similar to the flexible coupling. It consists of two pairs of pins. Each pair of pins is connected to a separate flexible clamp. Each of two samples (film/substrate or bulk) is squeezed between a respective pin pair and can be rotated around the pin-to-pin axis with a low predetermined friction. The clamp for the top sample is connected to the inner tube of the slider. The bottom sample clamp is connected to the outer tube. The rotation axes of the both samples are perpendicular to each other, in order that a full parallelism of their face surfaces can be achieved by bringing the films into contact for self-alignment.

The Coupling Probes are two half-wavelength antennas which provide contactless and variable coupling to the resonator.

During the measurement procedure, the samples are first pressed against each other for parallel self-positioning of their face surfaces. The sample is moved away from such contact up to 100–150 $\mu$m separation with the 0.1–1 $\mu$m increments. At each increment, measurements of the resonance frequency and Q-factor of the resonator vs. the separation value are made for further processing in accordance with theoretical formulas in order to extract the absolute values of $\lambda$ and $R_S$, which may be further used to determine other parameters of the samples such as absolute complex conductivity surface impedance, etc.

These and other novel features and advantages of this invention will be fully understood from the following detailed description of the accompanying drawings.

Table 1. Fitting parameters and theoretical predictions for the Cu and HTS VSPPRs: wherein f-fit—fitting of the frequency vs. dielectric spacer thickness data; Q-fit—fitting of the Q-factor vs. dielectric spacer thickness data; MI—mutual inductance measurements; BCS-fit—data obtained in accordance with BCS theory; theory—data obtained in accordance with the electrodynamics theory of the VSPPR.

Figure 2:
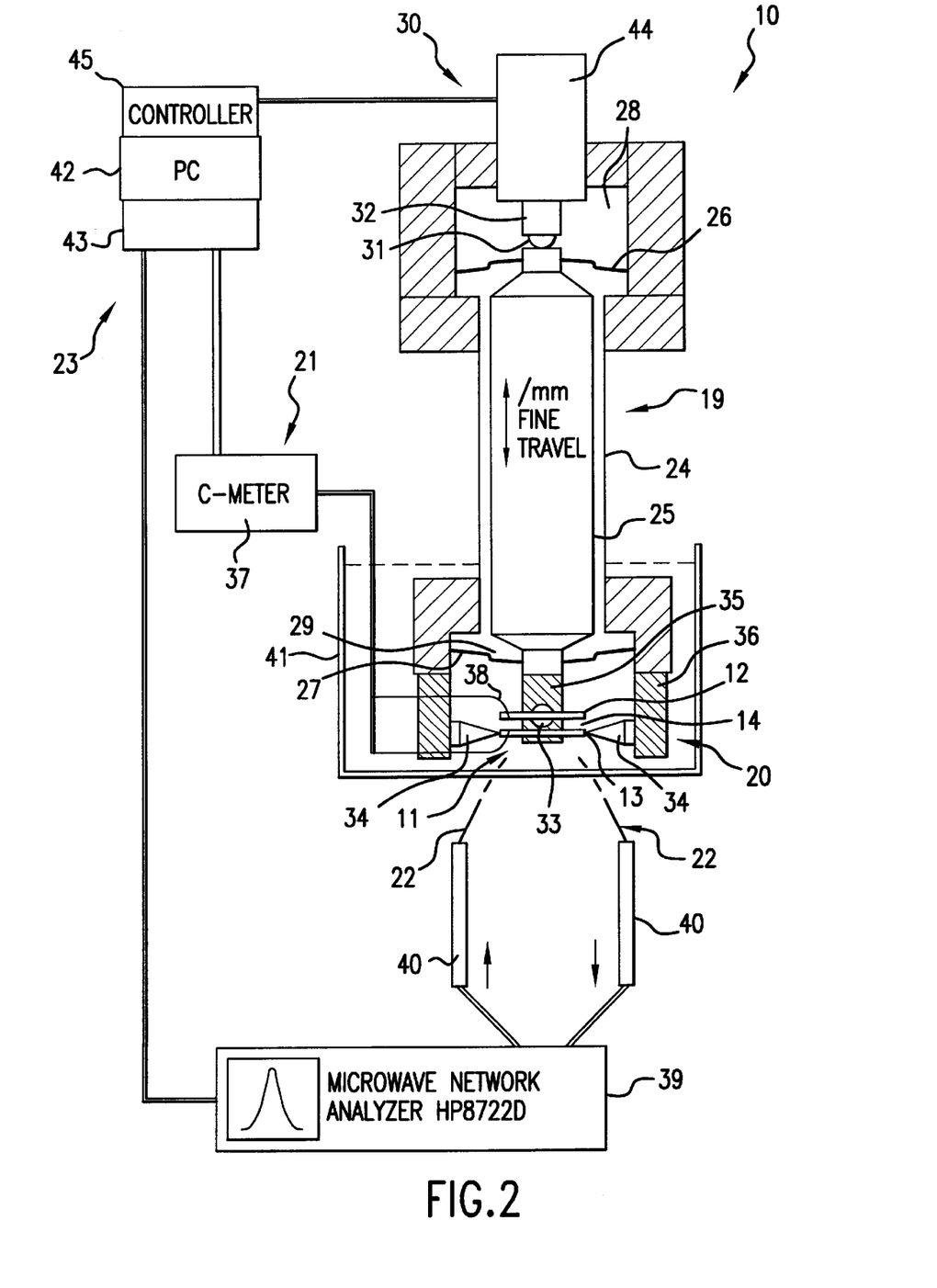
FIG. 2 is a schematic representation of the VSPPR system of the present invention.

The linear actuator 30 may be any kind of commercially available motorized micrometer head with appropriate specifications (full travel at least 1 mm, resolution 0.1 μm or

TABLE 1

| | | $\delta_{sk}$ or $\lambda$, nm | | | | | $f_0$, GHz | | L, cm | | $R_S$, $\mu\Omega$ | 1/$\beta$, cm | | | $s_0$, $\mu$m | |
|---|---|---|---|---|---|---|---|---|---|---|---|---|---|---|---|---|
| Sample | T, K | f-fit | Q-fit | MI | BCS-fit | theory | f-fit | theory | f-fit | theory | Q-fit | Q-fit | theory | | f-fit | Q-fit |
| Cu | 300 | 790 | 770 | n/a | n/a | 680 | 12.92 | 12.52 | 0.41 | 1.197 | — | 1.05 | 1.197 | | −1.67 | 1.51 |
| | 77 | 400 | 440 | n/a | n/a | 225 | 10.80 | 10.39 | 0.42 | 1.197 | — | 1.09 | 1.197 | | −3.49 | 1.00 |
| YBCO | 77 | 257 | n/a | 300 | — | — | 12.55 | 12.46 | 0.59 | 0.998 | 200 | 0.35 | 0.998 | | −0.38 | 0.46 |
| GBCO | 77 | 400 | n/a | 390 | 344 | — | 11.45 | 11.67 | 1.06 | 1.065 | 190 | 3.3 | 1.065 | | 2.55 | 3.33 |

DESCRIPTION OF THE PREFERRED EMBODIMENTS

Figure 1:
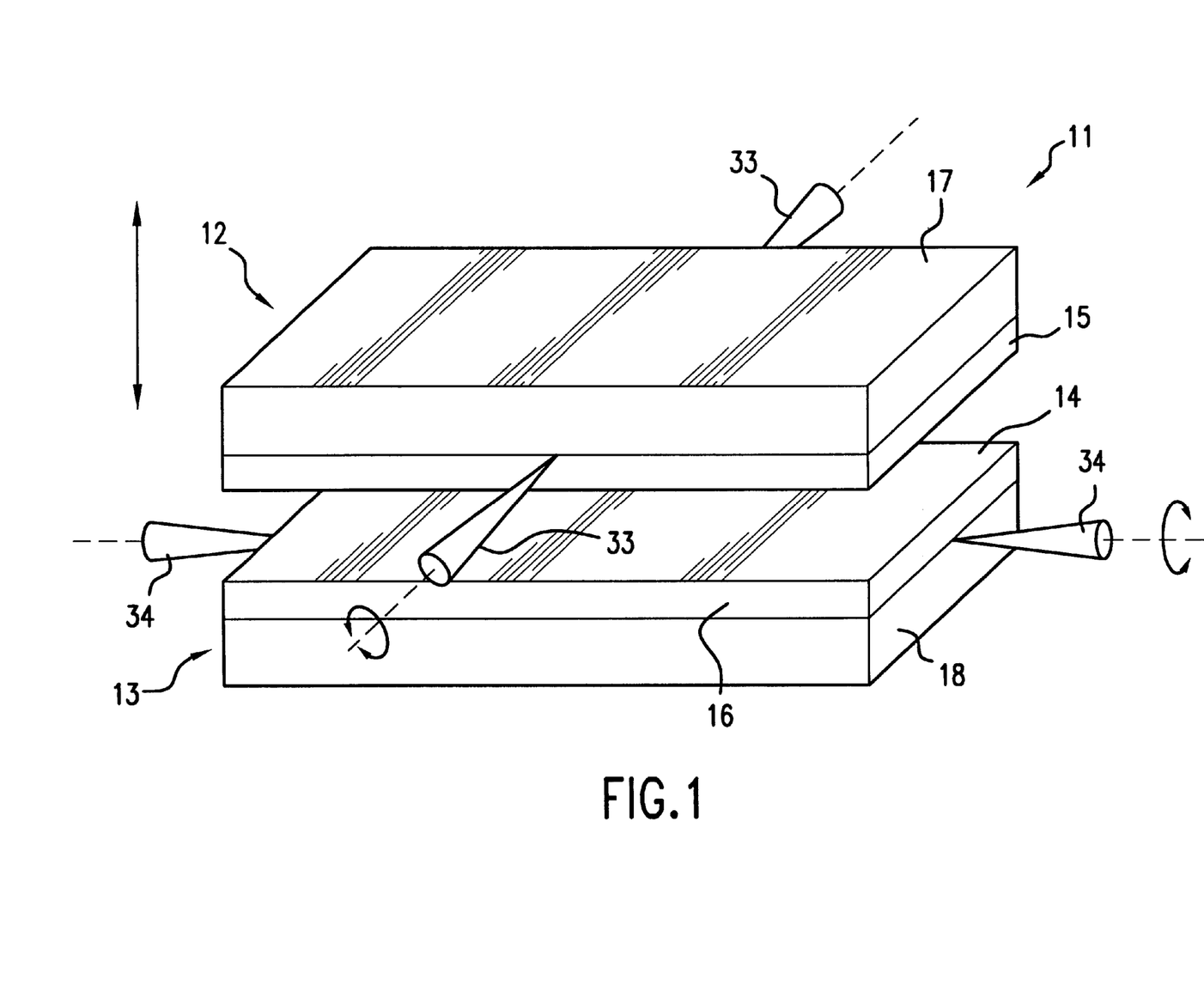
FIG. 1 shows schematically a geometry of the variable spacing parallel plate resonator (VSPPR) installed in the aligner with the liquid nitrogen or air filling the dielectric spacer.

Referring to FIGS. 1 and 2, there is shown apparatus 10 for measurement of penetration depth and absolute surface resistance, (as well as for determination of absolute complex conductivity and surface impedance) of metals and superconductors which includes a variable spacing parallel plate resonator 11, also referred to herein as VSPPR, formed by two parallel metallic or superconducting plates 12 and 13 separated by a thin dielectric spacer 14 which forms an open ended transmission line resonator. The plates 12 and 13 may be formed of metallic or superconducting material in the form of bulk material or thin films 15 and 16 deposited on respective dielectric substrates 17 and 18. The dielectric spacer 14 may be filled with liquid nitrogen, Liquid Helium, Vacuum, or air which allows continuous variability of its thickness from zero to several hundred microns. For plates 12 and 13 with linear dimensions on the order of 1 cm, the resonant frequency of the lowest operating TM01-mode is in the range of 10–15 GHz.

Apparatus 10 further includes a cryogenic linear Z-stage (cryogenic slider) 19 for moving the resonant plates 12 and 13, a films aligner 20 to maintain the plates 12 and 13 parallel and planarly aligned, in situ capacitance micrometry 21 to directly measure the separation and to monitor the parallelism of the plates 12 and 13 during the measurement. The apparatus 10 further includes microwave coupling probes 22 to excite the resonator 11 as well as associated electronics 23 for controlling the elements of the apparatus 10 for processing and analyzing the results of the measurement.

The cryogenic slider 19 is formed of two co-axial thin-walled stainless steel tubes 24 and 25 with diaphragm-type flexure bearings 26 and 27 incorporated between the inner tube 25 and the outer tube 24 at the top end 28 and bottom end 29 of the slider 19. The bearings 26 and 27 are formed from Be/Cu foil and operate at both room and cryogenic temperatures. They provide 1 mm of full travel, while substantially reducing friction, giving high stability to the slider 19 and theoretically providing resolution limited only by thermal fluctuations. Additionally they provide a preload for the inner tube 25 which is translated by a linear actuator 30 attached to the top end 28 of the slider 19 while the outer tube 24 is maintained stationary. The top end 28 of the slider 19 is maintained at room temperature, while the bottom end 29 may be immersed into a liquid nitrogen bath to obtain cryogenic conditions (14÷77 k). To reduce the effects of thermal contraction, the tubes 24, 25 have the same length and are formed from the same material (stainless steel). The slider 19 provides about 1 mm of fine rectilinear travel and gives minimal incremental motion down to 8.5 nm, limited only by the linear actuator 30.

better, accuracy better than 1%). The linear actuator 30 preferably is of the type having a non-rotating ball-shaped tip 31. It consists of a DC motor with 8.5-nm÷1 μm resolution rotary encoder driving a precision micrometer shaft 32 via a high-ratio backlash-free gear head (not shown).

The films aligner 20 consists of two pairs of pins 33—33 and 34—34 attached to two separate flexible clamps 35 and 36, respectively. From a kinematics point of view the films aligner 20 is similar to the flexible coupling. The clamps 35, 36 are formed by electrodischarge machining from a single piece of stainless steel. The pins 33—33 and 34—34 are made from Al or a sapphire stylus inserted into a cylindrical brass housing which is attached to a respective clamp 35 or 36. Each of the two VSPPR plates 12, 13 is squeezed between a respective pair of pins 33—33 or 34—34 and can be finely rotated around the pin-to-pin axis with enough friction to hold the plate in the designated position. Due to the fact that the rotation axes are perpendicular to each other, a full parallelism of the plates face surfaces can be achieved by bringing them into contact for self-alignment. The films aligner 20 also provides an in-plane alignment of the resonator plates 12, 13.

The clamp 35 holding the top plate 12 via the pins 33—33 is coupled to the inner tube 25 while the clamp 36 holding the bottom plate 13 via the pins 34—34 is coupled to the outer tube 24.

To perform a precise and accurate in situ monitoring of the dielectric spacer thickness (i.e. separation) between the resonator plates 12 and 13, a direct measurement of a 10 kHz capacitance between the plates 12, 13 is made by means of the capacitance micrometry 21 which includes a precision LCR-meter 37 with compensation for stray lead capacitance.

To connect each superconducting film 15, 16 to the LCR-meter 37, a 400-μm-wide and 200-nm-thick-gold strip on a Cr buffer layer may be evaporated through a 3D shadow mask onto two sides and the edge of the substrates 17 and 18. On the film side of each substrate 17, 18, the gold contact creates a small pad having an approximate area<0.1 mm² at one corner where the microwave current is close to zero. The contact continues over the edge of the substrate 17, 18 and on to the back side thereof, where a strip~7 mm long is deposited. The connection between the strips and the LCR-meter 37 leads is completed via 50-μm-thick gold wires 38, best shown in FIG. 2. A typical VSPPR has a capacitance in the range from 300–700 pF at the point of closest approach (depending on the dielectric constant and surface morphology of the samples) down to 8–10 pF at a separation on the order of 100 μm. To determine the spacer thickness, $s_c$, from the measured capacitance, C, the following expression, taking into account the fringe effects has been used:

$$c = \varepsilon_0\varepsilon_r\left\{\frac{Lw}{s_c} + L\left[0.4415 + \frac{1}{\pi}\left(\ln\frac{w}{s_c} + 1.451\right)\right] + \right.$$
$$\left. w\left[0.4415 + \frac{1}{\pi}\left(\ln\frac{L}{s_c} + 1.451\right)\right]\right\} \quad (1)$$

where L and w are the linear dimensions of the VSPPR plates 12 and 13, $\varepsilon_0 = 8.854 \cdot 10^{-12}$ F/m, and $\varepsilon_r = 1.454$ for a liquid nitrogen dielectric spacer.

The resolution of the capacitance micrometry 21 is estimated to be much greater than the 8.5 nm minimal incremental motion in the apparatus 10. The C value measured as a function of the displacement at separations from zero up to several microns is used to estimate the parallelism of the plates 12 and 13 which is routinely better than 1 mrad.

As described in previous paragraphs, the microwave measurements are carried out using two nominally identical samples with flat face surface—film and/or bulk metal and/or superconductor. The samples are brought together, face-to-face, sandwiching a thin dielectric separation (dielectric spacer 14) of variable thickness from 0 to 200 μm. Liquid Nitrogen, Liquid Helium, Vacuum, or a liquid or gas of unknown properties fills the dielectric spacer 14. This forms a 2-conductor parallel plate transmission line resonator 11, which can carry a quasi-TEM electromagnetic wave.

The Q-factor and resonant frequency of the resonator 11 are dictated by its geometry, as well as by the ratio between the dielectric spacer thickness and the screening (penetration) depth in the samples. The losses in the resonator are determined by: dielectric loss in the dielectric spacer matter, radiation losses, and the surface resistance of the samples. The first two contributions may be measured directly using a calibration procedure and/or eliminated by using disc-shape resonator with TM00i (where i is an integer) mode and vacuum dielectric spacer, and the measured Q-factors can be corrected to reflect only the contribution of the surface resistance losses.

The accurate estimation of the absolute value of the penetration depth λ and surface resistance $R_s$ is based on the simultaneous analysis of spacer thickness dependencies of the resonator frequency f and the Ohmic quality factor Q through a fit to the electrodynamics theory of the resonator as will be discussed in detail in the following paragraphs.

The microwave measurements are performed in the undercoupled regime by a HP8722D vector network analyzer (NWA) 39, best shown in FIG. 2. The built-in-3 db method is used to determine the resonance frequency and Q-factor of the resonator. The coupling probes 22, which are two antennas of 8–14 GHz bandwidth operationally engage the resonator 11 and are connected to the network analyzer 39 through semi-rigid coax cables 40 via a symmetrizing transition. The coupling probes 22 effectively excite the VSPPR 11 due to the similarity of the semi-circular shape of the antenna loop and the fringe quasi-static electric field at the resonator edge.

The probes 22 provide for a variable and contactless coupling to the resonator 11 and allows a study of resonators with Q-factors down to 60–70 in the conventional way of measurement, and down to 5–7 by using a unique digital NWA-based procedure developed for investigation of normal metal VSPPRs. According to the digital NWA-based procedure initially at the point of conducting contact between the plates 12 and 13, i.e., at zero separation, the S21 vs. frequency sweep is averaged and placed in the NWA's 39 memory. S21 is the complex transmission coefficient through the resonator. The NWA 39 is then switched to measure "data-memory" (i.e., the actual transmission characteristic with subtracted non-resonant background), and the top resonator plate 12 is moved away.

Averaging and smoothing are applied to the displayed "data-memory" characteristic and the resonance frequency and Q-factor are measured by the built-in-3 db method. The absence of a conductive enclosure in the setup of the present invention due to the use of a liquid nitrogen box 41 made of foam plastic avoids many systematic errors associated with the parasitic "package modes" found in conventional parallel plate resonator techniques.

The apparatus 20 is run by a personal computer (PC) 42 via GPIB interface 43, except for the micrometer head 44 of the linear actuator 30 which is operated by a PC-board controller 45. For measurements, the samples 12, 13 are installed at room temperature. The apparatus is then installed inside the cryostat and is cooled down to operating temperature. The samples are then positioned in parallel via self-alignment (easy pressing); and testing of the parallelism of the samples 12, 13 is made by measuring the capacitance vs. displacement of the samples relative to each other at room temperature as described in previous paragraphs.

In the case of cryogenic measurements, the bottom part of the apparatus 10 is immersed inside a liquid nitrogen bath 41. Once the samples 12, 13 and the slider 13 have reached thermal equilibrium with the bath 41, they are brought into contact and self-aligned again. In order to make the plates 12, 13 as close and as parallel as possible, the bottom portion of the apparatus 10 is vibrated at a frequency of 2–3 Hz while the plates 12, 13 are in contact. The VSPPR resonant frequency decreases, and the capacitance increases. The top plate 12 is then moved away, up to 100 μm–150 μm separation with increments of 10 nm to 1 μm (depending on the separation range) and the resonance frequency and Q-factor of the VSPPR vs. the displacement are measured at each increment.

To synchronize the microwave and capacitance data at each separation increment, the internal averaging of the capacitance is used by the LCR meter 37 during the time of the S21 vs. frequency sweep determined by the network analyzer 39. The total time for a single separation measurement is 2–3 sec. When the run is completed, the films are brought together again in order to check their parallelism.

The collected experimental data is further fit into electrodynamics theoretical formulae to extract absolute values of the penetration depth λ and surface resistance $R_s$ of the samples as will be discussed in further paragraphs.

For the sake of clarifying the processing of the experimental results, the electrodynamics of the VSPPR is briefly presented in the following paragraphs:

1. Propagation and Attenuation Constants in a Parallel Plate Transmission Line

As shown in FIG. 1, two superconductive or metallic plates 12 and 13 of thickness d and width w are separated by a dielectric spacer 14 of thickness s (s<<w) with complex permittivity $\varepsilon = \varepsilon_0\varepsilon_r(1-i\tan\delta)$ and permeability $\mu=\mu_0$. In the case of $|ks|<<1$ ($k=\omega\sqrt{\mu\varepsilon}$ is the complex wave number of the dielectric) only the slow-wave fundamental TM-mode exists between the plates 12 and 13. All fields vary as $\exp[i(\omega t - hz)]$, where $h=h_1-ih_2$ is the complex longitudinal wave number. Solution of Maxwell's equations in the space between the plates 12 and 13 taken together with the Leontovich impedance boundary condition (described in M. A. Leontovich, Investigations of Radiowave Propagation (Academy of Sciences, Moscow, 1948), Chapter 2), and are applied at the plates surface $$Z_{\it eff} = R_{\it eff} + iX_{\it eff} = \left(\frac{E_z}{H_x}\right)_{y=0} = -\left(\frac{E_z}{H_x}\right)_{y=-s} \quad (2)$$

yields the dispersion relation for the TM-mode:

$$\omega \in Z_{\it eff} = -i g \tan\frac{gs}{2} \quad (3)$$

where $Z_{\it eff}$ is the effective surface impedance of the plate, and $g=\sqrt{k^2-h^2}$ is the transverse wave number. Because $|Z_{\it eff}|<<\sqrt{\mu_0/\in}$ and $|ks|<<1$, the expansion of (3) yields:

$$h^2 = k^2\left(1 - i\frac{2Z_{\it eff}}{\mu_0\omega s}\right) \quad (4)$$

The accuracy of (4) is on the order of $|Z_{\it eff}/\sqrt{\mu_0/\in}|^2 <<10^{-4}$ for any actual experimental situation.

Separation of the real and imaginary parts in (4) gives the propagation and attenuation constants:

$$h_1^2 = k_0^2\varepsilon_r\left(1 + \frac{2X_{\it eff}}{\mu_0\omega s}\right) \times \left(\frac{1}{2} + \sqrt{\frac{1+\tan^2\delta}{4}\left[1+\left(\frac{2R_{\it eff}}{\mu_0\omega s + 2X_{\it eff}}\right)^2\right]} - \frac{R_{\it eff}\tan\delta}{\mu_0\omega s + 2X_{\it eff}}\right) \quad (5)$$

$$h_2 = \frac{k_0^2\varepsilon_r}{2h_1}\left(1 + \frac{2X_{\it eff}}{\mu_0\omega s}\right)\left[\frac{2R_{\it eff}}{\mu_0\omega s + 2X_{\it eff}} + \tan\delta\right] \quad (6)$$

where $k_0 = \omega\sqrt{\in_0\mu_0}$ is the vacuum wave number. The term in parenthesis is a correction to the propagation constant due to finite ohmic and dielectric losses.

2. Superconducting Transmission Line

The effective surface impedance of a finite thickness superconducting plate (film) 15, 16 of intrinsic impedance $Z_S = R_S + iX_S$, on a dielectric substrate 17, 18 of impedance $Z_{sub}$, within the approach $R_S << X_S$ and $d >> \lambda X_S/Z_{sub}$, is:

$$R_{\it eff} = R_s\left[\coth(d/\lambda) + \frac{d/\lambda}{\sinh^2(d/\lambda)}\right] + \frac{X_s^2}{Z_{sub}}\frac{1}{\sinh^2(d/\lambda)} \quad (7)$$

$$X_{\it eff} = X_s\coth(d/\lambda) = \mu_0\omega\lambda_{\it eff} \quad (8)$$

A high quality superconducting film of thickness $d >> \lambda X_S/Z_{sub}$ at temperature $T<0.95T_c$ and frequencies $<50$ GHz exhibits $R_{\it eff}/X_{\it eff} << 1$ ($R_{\it eff}/X_{\it eff} = 2R_S/X_S$ for $d<<\lambda$), and typically $\tan\delta \leq 10^{-3}$, so within the accuracy stated above, (5) and (6) yield:

$$h_1 = k_0\sqrt{\varepsilon_r}\sqrt{1 + \frac{2\lambda_{\it eff}}{s}} \quad (9)$$

$$h_2 = \frac{k_0\sqrt{\varepsilon_r}}{2}\sqrt{1 + \frac{2\lambda_{\it eff}}{s}}\left[\frac{2R_{\it eff}}{k_0(s+2\lambda_{\it eff})} + \tan\delta\right] \quad (10)$$

The loss correction in $h_1$ is omitted, which is valid for experimentally observed quality factors greater than 100.

3. Normal Metal Transmission Line

For the thick ($d >> \delta_{sk}$) metallic plate $Z_{\it eff} = \mu_0\omega\delta_{sk}(1+i)/2$ in the local limit, where $\delta_{sk}$ is the skin-depth. Because the minimum measurable Q-factor is >5 (i.e. $\delta_{sk}/(s+\delta_{sk}) \leq 5$) in our experiment and $\tan\delta \leq 10^{-3}$, an expansion can be employed in (5), which gives:

$$h_1 = k_0\sqrt{\varepsilon_r}\sqrt{1 + \frac{\delta_{sk}}{s}}\left[1 + \frac{1}{8}\left(\frac{\delta_{sk}}{s+\delta_{sk}}\right)^2\right] \quad (11)$$

$$h_2 = \frac{k_0\sqrt{\varepsilon_r}}{2}\sqrt{1 + \frac{\delta_{sk}}{s}}\left[\frac{\delta_{sk}}{s+\delta_{sk}} + \tan\delta\right] \quad (12)$$

4. Reflection from the Open Edge of the Semi-infinite Transmission Line

The VSPPR 11 has open ends, in contrast with the infinite line discussed above. Hence it is important to consider the fringe effects. The exact solution for the TEM-mode complex reflection coefficient $$R = -|R|\exp(-i\theta) \quad (13)$$

from the edge of a semi-infinite perfectly conducting parallel plate transmission line made from plates of zero thickness, in the case of $ks<<1$ gives:

$$|R| = \exp\left(-\frac{ks}{2}\right) \simeq 1 - \frac{ks}{2} \quad (14)$$

$$\theta = \frac{ks}{\pi}\left(1 - 0.5772 + \ln\frac{4\pi}{ks}\right) \quad (15)$$

These expressions are valid for the situation where the dielectric is the same inside and outside of the line and for infinitely wide plates.

5. Superconducting and Metallic VSPPRs

The complex resonance condition for a resonator of length L is:

$$\exp(-ihL) = R \quad (16)$$

Substitution of (13)–(15) and the complex angular frequency $\omega = \omega' + i\omega''$ into (16) and separation of real and imaginary parts yields:

$$h_1(\omega')L + \theta(\omega') = \pi \quad (17)$$

$$2h_2(\omega')L + s\omega'\sqrt{\mu_0\in_o\varepsilon_r} = \pi Q^{-1} \quad (18)$$

where the resonant frequency is defined as $\omega'/2\pi$, and the Q-factor is $\omega'/2\omega''$.

For the superconducting VSPPR, substitution of (9), (10) into (17), (18) gives the Eqs. (19)–(21) for the resonant frequency, fsc. Eq. (22) is obtained for the Q-factor, $Q_{SC}$, ignoring the energy stored in the fringe fields. This contribution is on the order of $s/L \leq 10^{-2}$. A similar procedure applied to the normal metal VSPPR by means of (11) and (12) for the longitudinal wave number, h, yields Eqs. (23) and (24), all of which will be described in further paragraphs.

It is important to discuss the applicability of Eqs. (19)–(24) for description of the actual VSPPR of finite width $w >> s$. The effects of the finite width on the propagation constant (5) and the ohmical Q-factor, can be estimated using Wheeler's principle as $\lambda[\delta_{sk}]/w \leq 10^{-4}$ and $s/w \leq 10^{-2}$, respectively. This is within the accuracy stated above. For the fringe effect terms in (19)–(24) it can be shown that in the case of $w >> s$, the finite width of the line affects (in the first approach) only the numerical values, but not the linear form of $|R|$ and $\theta$ dependencies (14), (15) on s. The power radiated from the side edges of the VSPPR 11 depends linearly on s as well. Hence such effects can be absorbed in the fitting procedure by the free parameters L and $\beta$ (shown in Table 1).

For the case of superconducting plates 12 and 13 the resonant frequency, fsc, depends on the plates linear dimension L, dielectric constant of the space 14 $\in = \in_0 \in_r$, dielectric spacer thickness s, effective penetration depth, $\lambda_{eff} = \lambda \coth(d/\lambda)$, of the electromagnetic field into the superconducting films of finite thickness d, and fringe effect:

$$fsc = \frac{f_0}{\sqrt{1 = 2\lambda_{eff}/s}} \frac{1}{1+\alpha s} \quad (19)$$

$$f_0 = \frac{c}{2L\sqrt{\varepsilon_r}} \quad (20)$$

$$\alpha = \frac{1}{\pi L}\left(0.423 + \ln\frac{2}{sf_0\sqrt{\mu_0 \varepsilon}}\right) \quad (21)$$

wherein $f_0$ is the resonant frequency of the perfectly conducting VSPPR with no fringe effect and $\alpha$ is the fringe effect geometrical factor. It can be seen from Eq. (19) that for the spacer thickness $s<(\lambda_{eff}/\alpha)^{1/2} \sim 30$ $\mu$m for $\lambda \sim 200$ nm, the penetration depth determines the reduction in the resonant frequency, while for thicker spacers 14, the resonant frequency is reduced by the fringe effect. Hence, a fit of experimental dependence of f(s) for s~0 to 100 $\mu$m to Eq. (19) can be used to determine $\lambda_{eff}$.

The unloaded Q-factor of the superconductive VSPPR, $Q_{SC}$ is determined by ohmic losses in the superconducting films 15, 16, dielectric losses in the dielectric spacer 14, and radiation losses:

$$\frac{1}{Q_{sc}} = \frac{1}{Q^\Omega} + \frac{1}{Q_d} + \frac{1}{Q_{rad}} \quad (22)$$

$$= \frac{R^*_{eff}}{\pi\mu_0 f^*(s+2\lambda_{eff})} \frac{fsc}{f^*} + \tan\delta + \beta s$$

Here $R_{eff}$ is the effective surface resistance (Eq. (7)) at fixed frequency f*, tan $\delta$ is the dielectric loss tangent, and $\beta=1/L$ is the radiation geometrical factor. The assumption that $R_S \alpha f^2$ for superconductors, i.e., $R_{eff}=R^*_{eff}(fsc/f^*)^2$, is used to derive (22). Eq. (11) takes into account the resonator energy stored in both kinetic and geometric inductances of the superconducting plates. For the spacer of thickness $s<(R_{eff}/\pi\mu_0 f\beta)^{1/2} \sim 20$ $\mu$m for $R_{eff} \sim 300$ $\mu\Omega$, Q is determined mainly by the ohmic losses, while for thicker spacers the radiation losses are dominant. A fit of the experimental dependence Q(s) to Eq. (22) yields the absolute value of $R_{eff}$.

In the case of the normal metal VSPPR the resonant frequency, $f_{NM}$, and Q-factor, $Q_{NM}$, are (in the local limit):

$$f_{NM} = \frac{f_0}{\sqrt{1+\delta_{sk}/s}}\left[1 - \frac{1}{8}\left(\frac{\delta_{sk}}{s+\delta_{sk}}\right)^2\right]\frac{1}{1+\alpha} \quad (23)$$

$$\frac{1}{Q_{NM}} = \frac{\delta_{sk}}{s+\delta_{sk}} + \tan\delta + \beta s \quad (24)$$

where $\delta_{sk}=2\rho/\omega\mu_0$ is the skin-depth and $\rho$ is the dc resistivity of the normal metal. In Eqs. (23) and (24) $\delta_{sk}$ is frequency dependent, i.e., $\delta_{sk}=\delta_{sk} f^*/f_{NM}$. Eq. (24) takes into account the resonator energy stored in geometric inductance of the normal metal plates. The frequency and Q-factor for Cu at room temperature have maximum values at $s \sim (\delta_{sk}/\beta)^{1/2} \sim 70$ $\mu$m, respectively. Fitting of the experimental dependencies for f(s) and Q(s) to the implicit functions (23) and (24) provides two independent estimates for the absolute skin-depth in the normal metal.

Experimental Results

To extract the absolute values of $\lambda_{eff}$ and $R_{eff}$ (or $\delta_{sk}$) from the experimental data, the latter have to be fit to the theoretical forms (19), (22) for the superconducting VSPPR or (23), (24) for the metallic one. The free parameters are $\lambda_{eff}$ or $\delta_{sk}$, $f_0$, and L in the denominator of Eq. (21) for the frequency data, and $R_{eff}$ or $\delta_{sk}$ and $\beta$ for the Q-factor data. Generally the tan $\delta$ value cannot be obtained from the fit since tan $\delta<<1/Q$.

In addition the following relationship between the exact dielectric spacer thickness, s, in (19)–(24) and the capacitively measured separation $s_c$ (in Eq. (1)) must be used:

$$s=s_c+s_0 \quad (25)$$

where $s_0$ is an additional free parameter in the fitting procedure. The nature of this offset will be discussed further with respect to Modeling of the real VSPPR. The parameter values for the fits are summarized in Table 1 and compared with theoretical predictions.

A. Normal Metal (CU) VSPPR

To ensure proper operation of the VSPPR technique, normal metal samples with a known value of the microwave skin-depth have been investigated. A pair of 0.7-mm thick OFHC Cu plates with an area of 9.88 by 11.97 mm² are used.

Figure 3:
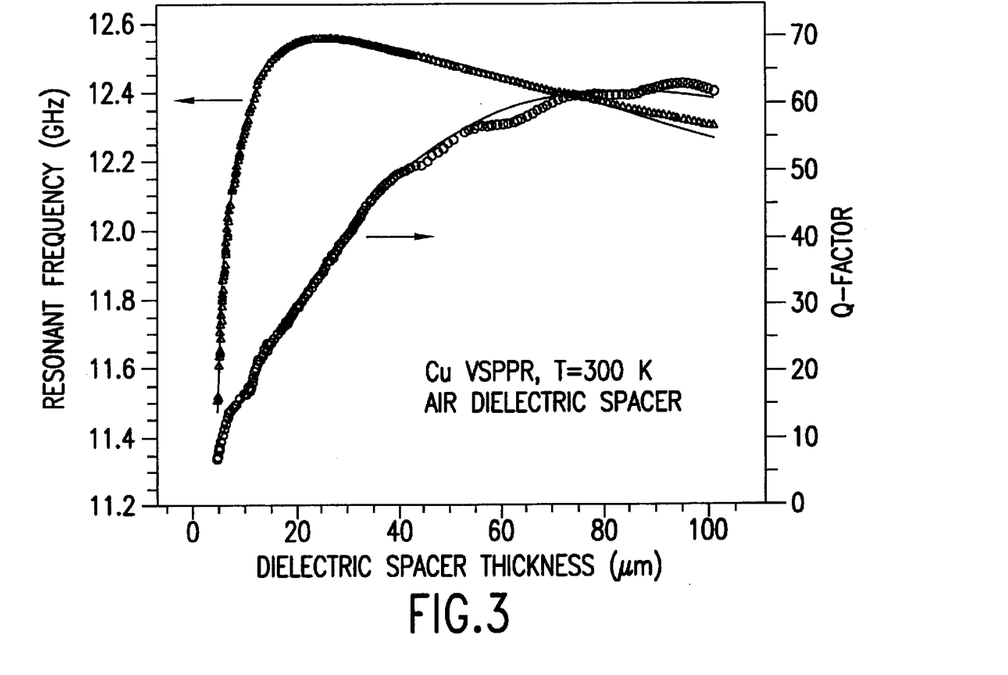
FIG. 3 is a diagram showing dependencies for the resonant frequency and Q-factor of Cu resonator vs. the dielectric spacer thickness in air at room temperature. The solid lines are the best fits to Eqs. (23) and (24) (parameter values for the fit are given in Table 1)
Figure 4:
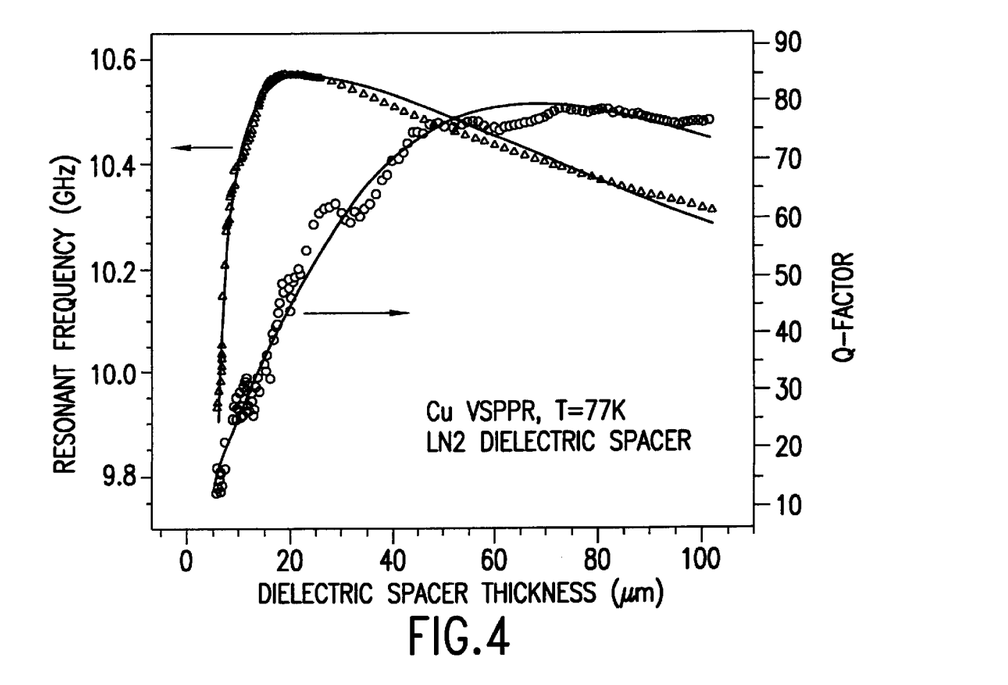
FIG. 4 is a diagram showing dependencies for the resonant frequency and Q-factor of Cu resonator vs. the dielectric spacer thickness at 77.35 K. The solid lines are the best fits to Eqs. (23) and (24) (parameter values for the fit are given in Table 1)

FIGS. 3 and 4 show the resonant frequency and Q-factor for the Cu VSPPR as functions of the thickness of air and liquid nitrogen dielectric spacer measured by capacitance micrometry at room and 77.35 K temperatures, respectively. The solid lines are the best fits to Eqs. (23) and (24). There is generally good agreement between the theory and experiment at small separations where the most important information about the skin-depth value is revealed. Some discrepancy at relatively large separations is observed due to the fact that the fringe effect theory used to derive (23) and (24) assumes that the resonator plates (12) and (13) have zero thickness and therefore does not provide a good description in the case of thick (i.e. much greater than s) elements serving as a flange for the fringe fields. The precision for determination of the resonant frequency and Q-factor of a Cu VSPPR is limited, especially at small separations, by the very low operating Q-factor~10. In addition, drift of the digitally subtracted background in the NWA transmission characteristic leads to a degradation of the data obtained at 77.35 K (FIG. 4).

At room temperature the 10 GHz skin-depth values obtained from the fitting procedures are $\delta^f_{sk}=0.79\pm0.1$ $\mu$m and $\delta^Q_{sk}=0.77\pm0.1$ $\mu$m from the frequency and Q-factor data, respectively. The values are close and in generally good agreement with the theoretical prediction of 0.68 $\mu$m based on a Cu electrical $\rho_{cu}=1.7$ $\mu\Omega$cm at 20° C.

The values for the skin depth are obtained at liquid nitrogen temperature at $\delta^f_{sk}(77 \text{ K})=0.40\pm0.1$ $\mu$m and $\delta^Q_{sk}(77 \text{ K})=0.44\pm0.1$ $\mu$m. The predicted 10 GHz skin-depth is 0.225 $\mu$m is based on a dc resistivity $\rho=0.2$ $\mu\Omega$cm at 77 K, which corresponds to $R_s=8.89$ m$\Omega$. However, at liquid nitrogen temperatures the microwave skin-depth in Cu becomes comparable with the mean free path of conducting electrons, leading to a strong dependence of the surface impedance on surface morphology. Hence the anomalous skin-effect approach has to be employed in (23) and (24) which is not part of the inventive concept as is herein described.

B. Superconducting VSPPR

1. $YBa_2C_3O_{7-x}$ Epitaxial Films

The samples are a pair of identical c-axis-oriented $YBa_2Cu_3O_{7-x}$ (YBCO) epitaxial films, grown by MOCVD on (100)-cut MgO single crystal dielectric substrates by STI, Inc., and cut from the same 2-inch-diameter wafer. The substrates are 0.5-mm-thick and the resonator effective area is 9.98 by 9.01 mm$^2$. The YBCO layer has a thickness of 760±30 nm, a critical temperature of 92.4 K, and a transition width of 0.25 K, as measured by AC susceptibility.

Figure 5:
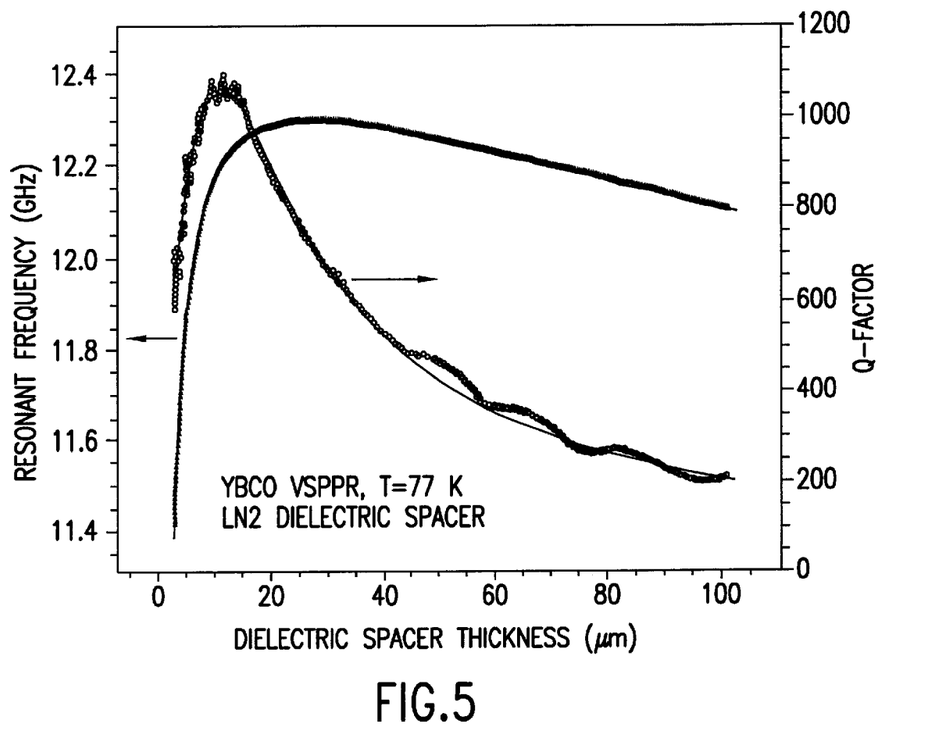
FIG. 5 is a diagram showing dependencies for resonant frequency and Q-factor for high $T_C$ superconducting $YBa_2Cu_3O_7$ resonator vs. the dielectric spacer thickness at 77.35 K. The solid lines are the best fits to Eqs. (19) and (22) (parameter values for the fit are given in Table 1)

FIG. 5 shows the experimental dependencies for the resonance frequency and the Q-factor of the YBCO VSPPR vs. dielectric spacer thickness measured by capacitance micrometry. The operating temperature is 77.35 K and liquid nitrogen is the dielectric spacer. The values obtained are $\lambda_{ab}$=257±25 nm and $R_s$=200±20 $\mu\Omega$ at 10 GHz. No finite thickness correction is necessary since the film thickness is 3 times larger than the penetration depth. Extrapolation of the 77 K $\lambda$ value down to zero temperature via an empirical two fluid model commonly accepted for HTS, $\lambda(T)=\lambda(0)\sqrt{1-(T/T_c)^2}$, gives $\lambda_{ab}(0) \approx 140$ nm, which is in generally good agreement with the literature data for high quality YBCO epitaxial films and crystals.

2. GdBa$_2$Cu$_3$O$_{7-x}$ Epitaxial Films

Figure 6:
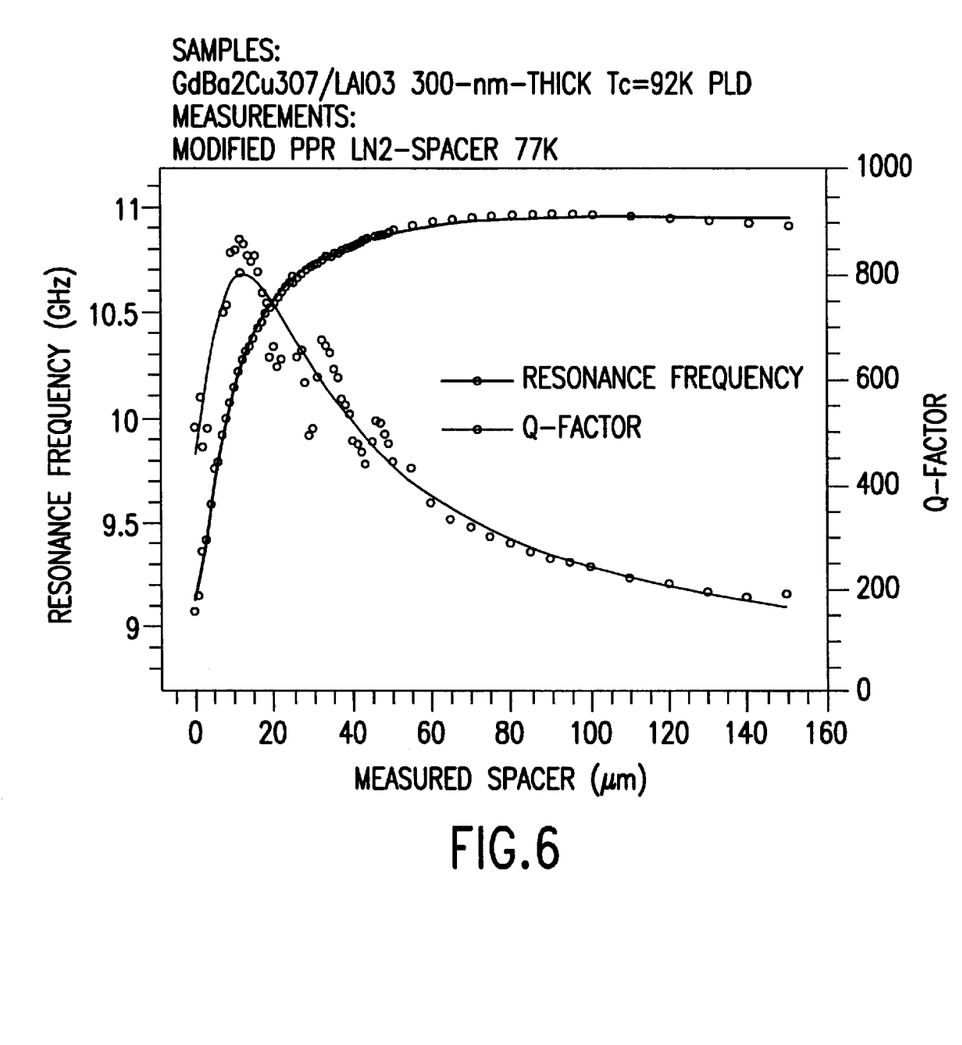
FIG. 6 is a diagram showing dependencies for resonant frequencies and Q-factor of $GdBa_2Cu_3O_7$ resonator vs. the dielectric spacer thickness at 77 K.

FIG. 6 shows experimental dependencies for the resonance frequency and Q-factor of High-T$_c$ Superconducting (HTS) resonator vs. dielectric spacer thickness. The operating temperature is 77 K and the dielectric spacer is Liquid Nitrogen. HTS samples are a pair of identical laser ablated GdBa$_2$Cu$_3$O$_7$ 300-nm-thick films on LaAlO$_3$ substrates of 10.6 to 7 mm linear dimensions, 20 mil in thickness. The resonant frequency and Q-factor dielectric spacer thickness dependencies are fit to theoretical forms. The parameters found from these fits are:

1) The effective magnetic penetration depth $\lambda_{eff}=\lambda$ coth (t/$\lambda$), where $\lambda$ is the magnetic penetration depth, t is the film thickness
2) Effective surface resistance $R_{eff} \approx 2R_s\lambda/t$, where $R_s$ is intrinsic surface resistance The fit parameters at 10 GHz, 77 K are: $\lambda_{eff}$=1.6±0.4 $\mu$m, $\lambda$=0.7±0.1 $\mu$m and $R_{eff}$=0.8±0.05 m$\Omega$ which is within an agreement with the commonly accepted data for ReBCO HTS films.

Comparison with Results Obtained by Other Techniques

The intrinsic ab-plane penetration depths for the YBCO and GBCO films may also be measured by the mutual inductance technique at 10 kHz. The values achieved for the two YBCO films are $\lambda_1$=297±5 nm and $\lambda_2$=304±10 nm at 77.35 K. To make a comparison with the raw VSPPR measurements, an average of the two penetration depths has to be made, i.e., $\lambda=(\lambda_1+\lambda_2)/2$=300±15 nm, which agrees with the VSPPR result. The values obtained for the two GBCO films are $\lambda_1$=377±11 nm and $\lambda_2$=403±12 nm at 77.35 K (note, that the errors do not include uncertainty in the films thickness). The average of two effective (due to finite film thickness d=300 nm) penetration depths is $\lambda_{eff}=[\lambda_1\coth(d/\lambda_1)+\lambda_2\coth(d/\lambda_2)]$=603±30 nm, which agrees with the VSPPR result. Therefore, these results establish that the VSPPR measurement of absolute penetration depth is valid.

The resonance frequency vs. temperature for a conventional parallel plates resonator (PPR) made from the GBCO films is measured as well. Two 12.5-$\mu$m- and 25-$\mu$m-thick Teflon™ films are used as dielectric spacers. The fit of the frequency vs. temperature data to s-wave BCS theory gives $\lambda_{ab}(0)$=197 nm and $\lambda_{ab}$(77 K)=344 nm. The latter is close to the VSPPR value. The observed difference may be due to an underestimation of the absolute $\lambda$ from the temperature fit due to some discrepancy between the data and BCS theory, and uncertainty in the Teflon spacer thickness. It should be pointed out that the dependencies for the change in the effective penetration depth measured at $s_{Teflon}$=12.5 and 25 $\mu$m agree with each other by assuming that s=$s_{Teflon}$+s*, with s*$\approx$5 $\mu$m. This value of s* is on the order of the measured non-flatness of these films as is discussed in further paragraphs.

Data Fitting and Experimental Complications

As described in previous paragraphs, the fitting of experimental data to the theoretical forms (19)–(24) has been used to extract the absolute values of $\lambda_{eff}$, $R_{eff}$ and $\delta_{sk}$. However, in practice the shapes of the resonator plates and the dielectric spacer are non-ideal. Therefore an evaluation has to be made as to the applicability of equations (19)–(24) for describing the real VSPPR and to estimate the errors which these imperfections introduce into the extraction of $\lambda_{eff}$, $\delta_{sk}$ and $R_{eff}$.

In general, it was found that the accuracy mainly depends on three factors: imperfections in the resonator shape, systematic error in capacitance micrometry, and the degree of agreement between the theory and experiment during the fitting procedure. Each such factor will be disclosed in more detail in the following description.

A. Imperfections in the VSPPR Shape

Non-flatness of the resonator plates (films) virtually always appears in practice. For instance, the average non-flatness of commercially available 1 cm$^2$ single crystal dielectric substrates for HTS thin films is about 0.5–2 $\mu$m, except for LaAlO$_3$ (LAO) which exhibits ~5–10 $\mu$m, as a result of going through the irreversible tetragonal-orthorhombic phase transition occurring at T~500° C. after the film deposition process. To image the non-flatness of the samples under study, a 1/20-wavelength optical flat was employed. A bump-like structure of the GBCO/LAO film surfaces with a lateral extent of 5–7 mm and a peak-to-valley height of 5–6 $\mu$m was observed. For the Cu plates and YBCO/MgO films the nonflatness was measured to be less than 5 $\mu$m and 1 $\mu$m across the sample, respectively. Thermal contraction between room and cryogenic temperatures and clamping forces may cause additional substrate deformation. Another possible imperfection is tilt of the resonator plates, which may be due to contamination on the plate surfaces and/or torsional deformation of the pins. The applicants have found experimentally that the tilt angle in the measurements is routinely less than 1 mrad.

Another imperfection in the VSPPR shape is an in-plane misalignment of the plates due to possible differences in their linear dimensions, their irregular shape, and the possible inability to have them in perfect alignment during installation into the clamps 35, 36. An estimate of the misalignment value is $\leq$100 $\mu$m for each resonator dimension.

The nonflatness and tilt affect the resonance frequency, Q-factor, and AC capacitance of the VSPPR. The in-plane misalignment affects the capacitance micrometry accuracy. Its effect on the resonant frequency is eliminated by using $f_0$ and L as free fitting parameters, while the ohmic Q-factor is shape independent and radiation Q-factor has a fitting parameter $\beta$ as well.

In the case of a square resonator, a degeneracy between the TM$_{01}$ and TM$_{10}$ modes occurs. In this case, the aforementioned imperfections in the resonator shape may provide a coupling between these nominally orthogonal modes, which may lead to splitting of the resonant frequencies.

B. Modeling of the Real VSPPR

To verify the applicability of equations (19)–(22) to extract $\lambda$ and $R_s$ from experimental data on non-ideal VSPPRs, and to estimate possible errors, a computer modeling of the real experimental situation dealing with a non-flat, tilted or in-plane misaligned VSPPR has been completed. Initially an electromagnetic model of the distorted VSPPR was created using the approach described in further paragraphs. Next, the "experimental" dependencies for resonant frequency, Q-factor and capacitance versus geometrical displacement between the resonator plates was generated and the data (i.e. parametric functions) was fit to the forms (19) and (22) with the error in the extracted $\lambda$ and $R_s$ being analyzed.

One can expect similar influences of non-flatness and tilt on the resonator properties, if they have comparable lateral and vertical geometrical scales. Thus, only the tilt of the resonator plates in the planes parallel and perpendicular to the $TM_{01}$ mode propagation direction was considered.

1. Data Generation Model for Tilted Resonator

A superconducting VSPPR was considered with in-plane aligned plates having surface impedance $Z_s=R_s+iX_s$, which are tilted by a small angle $\phi_0\ll1$, and ignore the fringe effect. To create an analytical model, a perturbation technique is employed, because the exact solution for such an inclined geometry does not exist for imperfect conductors (except for special cases). Within this approach the relationship between the complex resonant frequency of the superconducting (perturbed) resonator, $\omega_{sc}=\omega'_{sc}+i\omega''_{sc}$, and the resonant frequency of the perfectly conducting resonator of the same shape, $\omega_{pc}$, is:

$$\omega^{2sc} \simeq \omega^{2pc}\left(1+i\frac{Z_s}{\Gamma}\right) = \omega^{2pc}\left(1-\frac{X_s}{\Gamma}+\frac{R_s}{\Gamma}\right) \quad (26)$$

where $\Gamma=\mu_0\omega_{pc}G$ is the resonator geometrical factor and $$G = \frac{\int_V |\vec{H}|^2 dv}{\int_S |H_\tau|^2 ds} \quad (27)$$

where H is the magnetic field calculated for the perfectly conducting resonator, and $H_T$ its tangential component on the resonator walls. The integrals are taken over the whole resonator volume (inclined dielectric spacer) V and the walls (two plates) S. Hence, the dependence on tilt angle $\phi_0$ appears in (27) via the quantities V, H and $H_T$.

An untitled VSPPR has G=s/2, and the real part of Eq. (26) is just an expansion of the exact expression (19) for $\lambda/G\ll1$. Thus, in order to recover the exact values for the resonant frequency and ohmic Q-factor as $\phi_0\rightarrow0$, Eq. (26) is rearranged as follows:

$$\omega'_{sc} = \frac{\omega_{pc}}{\sqrt{1+\lambda/G}} \quad (28)$$

$$Q^{-1}_\Omega \frac{2\omega''_{sc}}{\omega'_{sc}} = \frac{R_S}{\mu_0\omega'_{sc}(G+\lambda)} \quad (29)$$

The capacitance to be "measured" by the capacitance micrometry 21 is approximated as $$C = \int_A (\varepsilon_0\varepsilon_r/s_{nu})da,$$

where $s_{nu}$ A is the nonuniform dielectric spacer thickness, the integral is taken over the resonator area A, and the capacitive dielectric spacer $s_c$ is given by Eq. (1). In order to fit the generated data to the forms (19) and (22) a linear relationship between s and $s_c$ is used as in Eq. (25).

2. Tilt in the Plane Parallel to the Mode Propagation Direction

The cylindrical coordinates are chosen so that the z-axis is perpendicular to the direction of the mode propagation, r, and parallel to the resonator plates. The magnetic field of the perfectly conducting resonator in (27) has only a z-component $(H_z(r)=B_1H_0^{(1)}(kr)+B_2H_0^{(2)}(kr)$, where $H_0^{(1)}(kr)$ and $H_0^{(2)}(kr)$ are the Hankel functions of a first and second kind, respectively, k is the wave number in the dielectric, and $B_1$ and $B_2$ are constants. The procedure described in the section "Data Generation Model for Tilted Resonator" has been performed for a VSPPR of area 1 cm² and penetration depth of 250 nm. It is found that in order to obtain an error in $\lambda$ of less than 10%, the tilt angle has to be less than 0.7 mrad. This tilt gives an overestimation of $\lambda$ and a negative offset value $|s_0|\leq 1.2\ \mu m$.

3. Tilt in the Plane Perpendicular to the Mode Propagation Direction

The cylindrical coordinates are chosen so that the z-axis is parallel to the direction of the mode propagation. The magnetic field in (27) has only an r-component. Based on the law of magnetic flux conservation $H_r(r,z)=D \sin(\pi z/L)/\phi_0 r$, where D is constant. For the same resonator as above it is found that an error in $\lambda$ of less than 10% is obtained if this type of tilt is less than 1 mrad. This gives underestimation of $\lambda$ and a negative offset value $|s_0|\leq \mu m$.

C. Accuracy of Capacitance Micrometry

While the precision of the capacitance micrometry is well above the requirements of the subject experiment, a systematic error in the capacitance value may noticeably contribute to the error in $\lambda$. By performing the modeling of an untitled VSPPR, as discussed with regard to "Modeling of the Real VSPPR", it was found that the estimated in-plane misalignment ~100 $\mu$m for each resonator dimension gives an error in the capacitance value due to imperfect compensation of the stray capacitance for the LCR meter 37 leads and/or uncertainty in the dielectric spacer permittivity (in the case of liquid nitrogen) is $\leq 2$ pF, which gives an error in $\lambda$ less than 6%.

Therefore, the three most common forms of VSPPR non-ideality and systematic error in capacitance micrometry give rise to errors in absolute $\lambda$ on the order of 10% or less for the experimental conditions of the technique of the present invention.

C. Microwave Coupling

It was also observed that strong coupling between the antennas 22 and VSPPR 11 may lead to some disagreement between the experimental data and the theory during the fitting procedure. Strong coupling distorts the resonator eigenfrequency and Lorentzian shape of the resonance curve due to the interaction between electromagnetic oscillations in the resonator 11 and standing waves in the coax cables 40. This interaction is stronger when the VSPPR and the standing wave resonances have comparable bandwidths. Another possible parasitic effect is the increase of the coupling as the plates separation increases. To eliminate the influence of these effects on the accuracy of the experiment, the coupling has to be minimized such that the insertion loss of the VSPPR is at least 35 to 40 dB.

E. Secondary Fitting Parameters

The secondary fitting parameters are presented in the Table I, such as the frequency of the perfectly conducting VSPPR with no infringe effect, $f_0$, fringe effect factors L and $\beta$, and offset in the dielectric spacer thickness $s_0$.

The discrepancy between the theoretical predictions and fitting values obtained for $f_0$ may be due to the following factors: in-plane misalignment of the resonator plates; disagreement between the experimental data and theory at large separations for the Cu VSPPR; the edges of the Cu plates not being perfectly square-shaped (unlike the HTS films on single crystal substrates), which causes the effective resonator length to be slightly shorter than the geometrical length; error in the value for microwave dielectric permittivity of Liquid Nitrogen.

The fitting parameters L and 1/β are usually smaller than predicted, which corresponds to an underestimate of the fringe effect geometrical factors from the electrodynamics theory for the VSPPR used to derive (19)–(24).

The $s_0$ values obtained from the frequency fits are on the order of −1 μm which agrees with the results of simulation for tilted VSPPR discussed in previous paragraphs.

The Variable Spacing Parallel Plate Resonator of the present invention and the method associated therewith to measure absolute values of the penetration depth and surface resistance in superconductive and metallic thin films of bulk samples was developed and penetration/skin depth and surface resistance values for HTS and Cu samples have been presented. The technique allows investigation of both thin films and bulk samples, and provides absolute values for $R_s$ and λ in the same experiment, at the same frequency and temperature. Their extraction from the experimental data is based on a straightforward electrodynamic description of the resonator with no assumptions about the nature of the superconducting state being made. Capacitance micrometry is utilized to directly measure the separation between the resonator plates and to reduce the effect of tilt and non-flatness on the accuracy of the measured $R_s$ and λ. The VSPPR is fully compatible with the conventional parallel plate resonator technique which allows one to obtain the temperature dependence of $R_s$ and λ, which results in the full complex conductivity of the superconductor being constructed.

The VSPPR is operated in a wide range of temperatures including room and cryogenic temperatures. The use of flexure stage and direct capacitance micrometry eliminates the influence of the cryogenic environment on the performance of the system, and allows the existing micropositioning setup to be adapted for 4.2 K operation. An active films aligner may decrease the tilt and enhance the accuracy of the technique. To improve the performance of the fitting procedure a 3D electromagnetic simulation of the real VSPPR (including substrates) followed by development of an analytical calculation for the resonant frequency, Q-factor and AC capacitance may be accomplished.

In different embodiments envisioned to be within the full scope of the invention, the following alternative structural elements can be used.

1) Other types of the flexure bearings
2) Other types of the Film Aligner
3) Variable temperature version (4–300 K of the apparatus 10
4) Vacuum dielectric spacer of the resonator
5) Disc resonator with the TM001 mode to eliminate radiation losses and fringe effects
6) Direct measurements of the dielectric spacer thickness may be made by using of the parallel plate resonator as an optical Fabry-Perot resonator
7) A vibration source may be installed at the bottom of the slider 19 to reduce the static friction in the Aligner 20 and so to improve the alignment of the films.

The present invention in addition to the applications described in the previous paragraphs may find utility in:

1. Standard for microwave complex surface impedance (surface resistance and surface inductance) of metals and superconductors.

Establishment of a surface resistance standard is an important issue for HTS film applications in wireless communications. Currently there are two techniques, namely a (conventional) parallel plate resonator and a dielectric resonator, as contestants in the race to become a standard for characterization of HTS films for microwave applications. It is believed that the VSPPR technique can fill this role as well. The definition can be done in terms of a frequency and a length: an effective surface resistance of 100 μΩ at 10 GHz is a FWHM=2.533 MHz of the resonance curve for the ohmic Q-factor produced by the VSPPR with an effective separation between the plates $s_{eff}=s+2\lambda_{eff}=10$ μm. Note, that the VSPPR's ohmic Q-factor (and so the FWHM above) is independent of the sample geometry and mode number.

2. Automated tool for measurements of microwave surface resistance and absolute penetration depth in normal metal and superconducting films.

3. Apparatus to measure dielectric permittivity and loss tangent of liquid and gas dielectrics at microwave frequency.

4. Tunable microwave oscillator/bandpass filter.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:

1. An apparatus for determining absolute values of penetration depth and surface resistance of a sample at microwave frequencies, comprising:

a resonant structure formed of a pair of substantially identical samples positioned in substantially parallel relationship each with respect to the other and sandwiching a dielectric spacer therebetween, displacement means adapted for displacing at least one of said samples with respect to another one of said samples for varying a thickness of said dielectric spacer disposed therebetween, measuring means for measuring the resonant frequency and the quality factor of said resonant structure versus said variable thickness of said dielectric spacer, and processing means coupled to said measuring means for processing said measured resonance frequencies and the quality factors versus said variable thickness of said dielectric spacer, said processing means including means for extracting absolute values of penetration depth and surface resistance for said samples, each of said means for extracting being correlated with a type of said samples.

2. The apparatus of claim 1, wherein said samples are of superconducting nature, and wherein said means for extracting includes means for calculating resonant frequency of a resonator, and a fringe effect in accordance with:

$$f_{sc} = \frac{f_0}{\sqrt{1 + 2\lambda_{eff}/s}} \frac{1}{1 + \alpha s}$$

$$f_0 = \frac{c}{2L\sqrt{\epsilon_r}}$$

$$\alpha = \frac{1}{\pi L}\left(0.423 + \ln\frac{2}{s f_0 \sqrt{\mu_0 \epsilon}}\right)$$

wherein $f_{sc}$ is a resonant frequency of the resonator, $f_0$ is the resonant frequency of the perfectly conducting VSPPR with no fringe effect, α is the fringe effect geometrical factor, S is a thickness of the dielectric spacer, L is the linear dimension of the samples, $\epsilon = \epsilon_0 \epsilon_r$ is a dielectric constant of the dielectric spacer, $\lambda_{eff}$ is an effective penetration depth, $\mu_0$ is the permeability of free space, $Q_{sc}$ is the Q factor of the superconducting resonator, $R_{eff}$ is the effective surface resistance at fixed frequency f, tan δ is the dielectric loss factor, and β=1/L is the radiation geometrical factor.

3. The apparatus of claim 1, wherein said samples are of metallic nature, and wherein said means for extracting include means for calculating a resonant frequency and a factor of a metal resonator include:

$$f_{NM} = \frac{f_0}{\sqrt{1+\delta_{sk}/s}}\left[1 - \frac{1}{8}\left(\frac{\delta_{sk}}{s+\delta_{sk}}\right)^2\right]\frac{1}{1+\alpha s}$$

$$\frac{1}{Q_{NM}} = \frac{\delta_{sk}}{s+\delta_{sk}} + \tan\delta + \beta s$$

Wherein $\delta_{sk}=\sqrt{2\rho/\omega\mu_0}$ is the skin-depth,

ρ is the dc resistivity of the normal metal, $f_{NM}$ is the resonant frequency, S is the thickness of the dielectric spacer, α is the fringe effect geometric factor, $f_0$ is the resonant frequency of the perfectly conducting VSPPR with no fringe effect, $Q_{nm}$ is the Q factor of the metal resonator, tan δ is the dielectric loss factor, and β is the radiation geometrical factor.

4. The apparatus of claim 1, wherein each said sample includes a bulk material.

5. The apparatus of claim 1, wherein said dielectric spacer includes either one of Liquid Nitrogen, Liquid Helium, Vacuum and air.

6. The apparatus of claim 1, further including microwave antennas operatively coupled to said resonant structure for resonating same.

7. The apparatus of claim 1, further including a bath containing a material maintained at cryogenic temperature, said resonant structure being immersed into said bath for cryogenic measurements.

8. The apparatus of claim 1, wherein said measurements are made in steps at each 10 nm÷1 μm separations between said samples, with the maximum separation therebetween up to approximately 100 μm.

9. The apparatus of claim 1, wherein each said sample includes a film.

10. The apparatus of claim 9, wherein each said sample further includes a dielectric substrate, said film being deposited on a surface of said dielectric substrate, said films of each of said samples being disposed in facing relationship each with respect to the other.

11. The apparatus of claim 1, further including means for measuring capacitance between said samples to monitor the thickness of said dielectric spacer.

12. The apparatus of claim 11, wherein said means for measuring the capacitance between said samples include means for estimating parallelism between said samples.

13. The apparatus of claim 1, wherein said displacement means includes a first coaxially disposed tube and a second coaxially disposed tube, and an actuator mechanism operatively coupled to said first tube to slide said first tube longitudinally within said second tube, said first tube being operatively coupled to one of said samples, said second tube being operatively coupled to a differing one of said samples, said processing means being coupled to said actuator mechanism for controlling the distance and the direction of said first tube displacement within said second tube, thereby controlling the thickness of said dielectric spacer between said samples.

14. The apparatus of claim 13, wherein said first and second tubes are formed of stainless steel and are of substantially the same length.

15. The apparatus of claim 13, further including a samples aligner, said samples aligner including first and second pairs of coaxial pins, a pin-to-pin axis of said first pair of the pins extending substantially perpendicularly to a pin-to-pin axis of said second pair of the pins, each pair of said pins flexibly engaging a respective one of said samples at displaced points thereof thereby allowing sample rotation about a respective pin-to-pin axis, said first pair of the pins being operatively coupled to said first tube, and said second pair of the pins being operatively coupled to said second tube, said processing means for controlling said actuator to bring said samples into intimate contact therebetween for self-alignment.

16. A method for determining absolute values of penetration depth and surface resistance of a sample at microwave frequencies, comprising the steps of:

forming a resonant structure having a pair of substantially identical samples under investigation positioned in substantially parallel relationship each with respect to the other and separated by a variable thickness dielectric spacer disposed therebetween, displacing one of said samples with respect to another one of said samples, measuring resonance frequencies and quality factors of said resonant structure versus the thickness of said variable dielectric spacer, and processing said measured values in accordance with predetermined calculated parameters correlated with each type of said samples to extract therefrom absolute values of penetration depth and surface resistance for said samples.

17. The method of claim 16, further including the steps of:

measuring capacitance between said samples for monitoring the thickness of said dielectric spacer and for testing parallelism between said samples.

18. The method of claim 16, further including the steps of:

displacing said samples each with respect to the other in predetermined increments of 10 nm÷1 μm up to 100 μm separation, and making measurements at each increment displacement with the total time for each measurement in the range of 2–3 sec.

19. The method of claim 16, further including the steps of suspending each of said samples on a respective clamp providing a kinematically flexible coupling therebetween, and self-aligning said samples by bringing them into intimate contact therebetween.

20. The method of claim 19, further including the step of:

vibrating said samples suspended on said clamps at the frequency of 2–3 Mz to enhance the parallelism therebetween.

* * * * *